United States Patent [19]

Sugai et al.

[11] 4,218,216
[45] Aug. 19, 1980

[54] METHOD OF LUBRICATING DENTAL HAND-PIECE AND SMALL-SIZED OILER FOR USE THEREIN

[75] Inventors: Hiroshi Sugai; Haruo Ogawa, both of Kyoto, Japan

[73] Assignee: Kabushiki Kaisha Morita Seisakusho, Kyoto, Japan

[21] Appl. No.: 923,544

[22] Filed: Jul. 11, 1978

[30] Foreign Application Priority Data

Jul. 12, 1977 [JP] Japan ................................ 52-83751

[51] Int. Cl.² ............................................. A61C 11/00
[52] U.S. Cl. ................................................. 433/104
[58] Field of Search ................... 32/26, 27; 184/55 A

[56] References Cited

U.S. PATENT DOCUMENTS

| 3,595,342 | 9/1969 | O'Leary | 184/56 A |
| 3,682,274 | 8/1972 | Bennett | 184/55 A |
| 3,946,490 | 3/1976 | Sotman | 32/28 |

Primary Examiner—Robert Peshock
Attorney, Agent, or Firm—Koda and Androlia

[57] ABSTRACT

A method of lubricating a dental hand-piece wherein a small-sized lubricating oil sealed oiler is detachably mounted in a position adjacent to the rotor side of a rotor driving air passageway of a dental hand-piece device, the lubricating oil from said oiler is continuously mixed into rotor driving air to atomize said oil by utilizing the pressure and flow rate of said rotor driving air when said hand-piece is in use, and the mist oil thus obtained is supplied together with said air to said rotor to thereby continuously lubricate the rotor; and a novel small-sized oiler used in the method; are disclosed.

8 Claims, 4 Drawing Figures

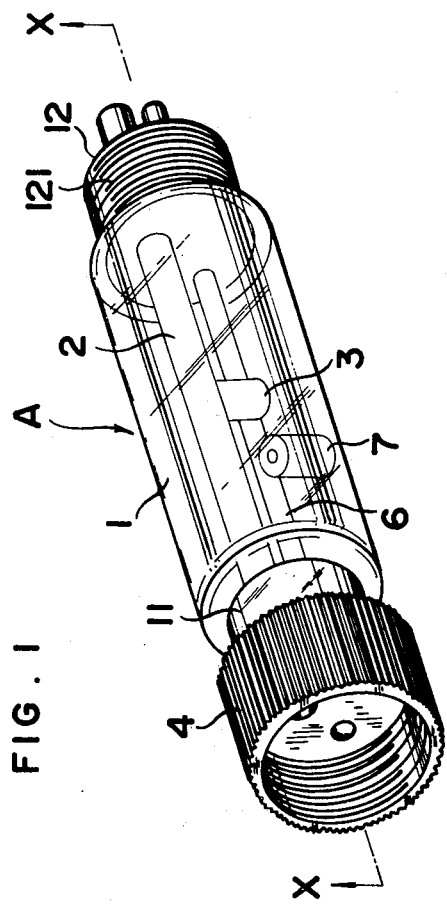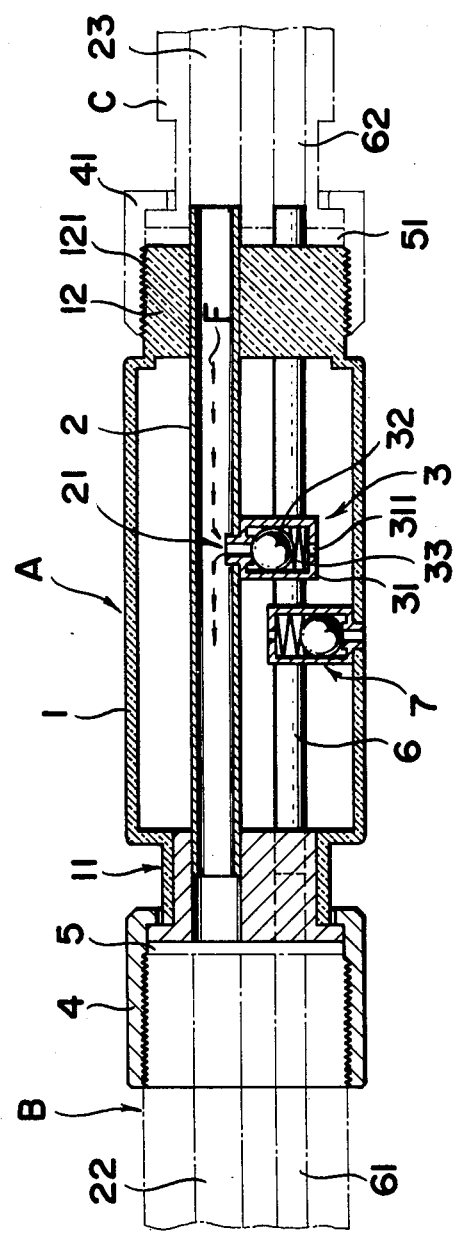

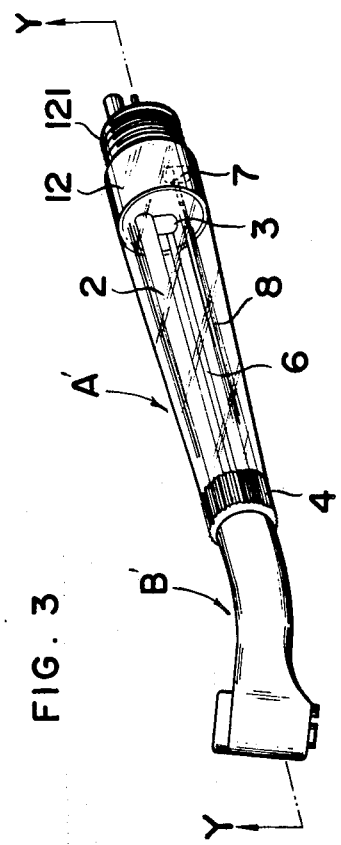
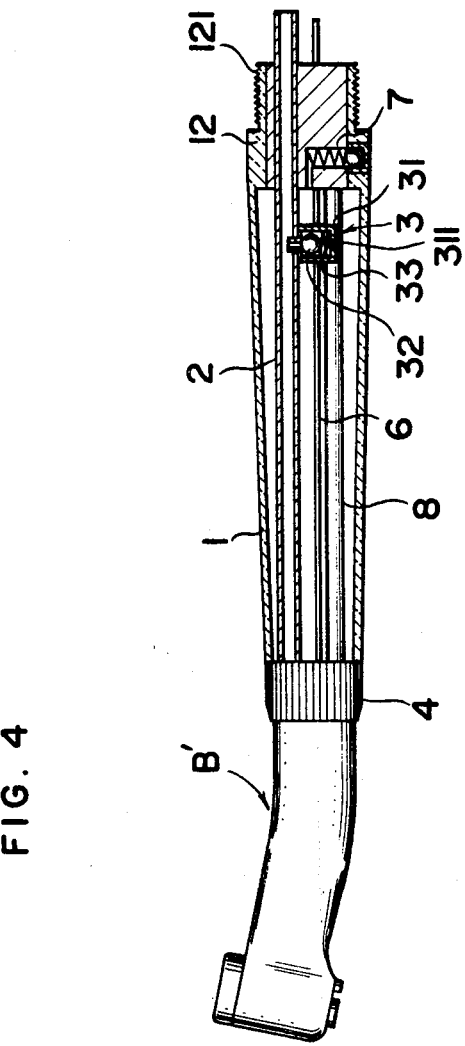
FIG. 3
FIG. 4

METHOD OF LUBRICATING DENTAL HAND-PIECE AND SMALL-SIZED OILER FOR USE THEREIN

BACKGROUND OF THE INVENTION

1. Field of the Invention

This invention relates to a novel method of lubricating a dental hand-piece and a novel small-sized oiler directly used in the method.

2. Prior Art

As well known, a dental hand-piece is roughly classified into two types, one being a hand-piece whose rotor bearings are of a ball bearing type and the other being a hand-piece whose rotor bearings are of an air bearing type. Lubrication of the ball bearing type hand-piece is carried out either by a so-called mist lubrication method by which mist oil is mixed into rotor driving air and the air is then fed to the rotor, or by sealing the bearing with grease. However, from the viewpoint of the durability of the bearing, the mist lubrication is more advantageous and hence most of the lubrication methods have recently been changing to the mist lubrication method.

According to the mist lubrication heretofore in use, a large-sized oil atomizer is connected to a rotor driving air feed passageway inside the base of a dental treatment chair, and lubricating oil is intermittently dropped from an oil atomizer onto the rotor driving air passing through the air feed passageway and is thus mixed into the air, and finally the rotor driving air having the mist oil thus mixed therewith is fed to the rotor. But such a mist lubrication method poses the following problems yet to be solved. Namely, firstly, because the oil atomizer intermittently atomized and feeds lubricating oil, it merely effects intermittently. Secondly, because the oil atomizer is disposed generally in such an out-of-eyeshot place as inside the base of the treatment chair, there is a tendency of the hand-piece to be used before oil shortage is noticed and to cause trouble such as seizure of rotor. Thirdly, because the oil atomizer is large in size and high in price, it is disadvantageous in point of installation space and cost. Forthly, oil change work for the oil atomizer is not easy. Fifthly, because an air bearing type hand-piece cannot be connected to the rotor driving oil feed passageway having the oil atomizer connected thereto, a separate rotor driving passageway for exclusive use in the air bearing type hand-piece must be provided when the air bearing type hand-piece is used in combination with the ball bearing type hand-piece.

SUMMARY OF THE INVENTION

It is an object of the invention to provide a unique mist lubrication method capable of solving the above-described problems once for all.

It is another object of the invention to provide a small-sized oiler adapted to be directly used in the method.

These and other objects and advantages of the invention will become apparent for persons skilled in the art from the following description.

BRIEF DESCRIPTION OF THE DRAWINGS

FIG. 1 is a perspective view of one embodiment of the small-sized oiler of the invention;

FIG. 2 is an enlarged longitudinal sectional view taken along line X—X of FIG. 1;

FIG. 3 is a perspective view of another embodiment of the oiler of the invention; and FIG. 4 is a partial longitudinal sectional view taken along line Y—Y of FIG. 3.

DESCRIPTION OF THE PREFERRED EMBODIMENTS

The small-sized oiler A shown in FIGS. 1 and 2 is a type of oiler adapted to be detachably attached to the rear end of a dental hand-piece, the type being among those small-sized oilers according to the invention. Namely, this small-sized oiler A comprises mainly a substantially cylindrical oil case 1 closed at both ends, an air feed pipe 2 loosely inserted into and fixed to the case 1, and a check valve 3 disposed in an oil port 21 of the pipe 2. In the projecting portion 11 formed at one end of the oil case is slidably engaged with a cover nut 4 in a manner that it may not fall out. As shown in FIG. 2, the small-sized oiler A is constructed to be detachably mounted to the dental hand-piece by threadedly fitting the cover nut 4 over the rear end portion of the hand-piece B preferably through a suitable packing. On the outer periphery of a thick-walled portion 12 at the other end of the oil case 1 is formed a threadedly mating face 121 so as to be detachably connected to a flexible hose C by means of a cover nut 41 at the end of the hose preferably through a suitable packing 51. And the feed pipe 2 inside the oil case 1 is connected coaxially with air feed pipes 22 and 23 built in the hand-piece B and in the flexible hose C respectively and rotor driving air is fed from the air feed pipe 23 through the air feed pipe 2 and air feed pipe 22 to the rotor. Also, the small-sized oiler A as illustrated in FIGS. 1 and 2 has a water feed pipe 6 for flushing and cooling loosely inserted through and fixed to the oil case 1 thereof, the water feed pipe 6 being connected coaxially with water feed pipes 61 and 62 incorporated in the hand-piece B and the flexible hose C respectively, and flushing or cooling water is fed from the pipe 62 through pipe 6 and pipe 61 to the hand-piece B and is jetted from another end of the hand-piece.

On the other hand, the check valve 3 which constitutes the essential part of the oiler of this invention is of the conventional construction, as shown in FIG. 2, and comprises a check valve case 31 equipped with an oil port 311, a ball valve 32 and a coil spring 33 mounted inside the case 31. The spring pressure of this coil spring 33 is adjusted to satisfy the following condition. Namely, in case the spring pressure of the coil spring 33 is $P_1$, the pressure of the rotor driving air inside the air feed pipe 2 when the hand-piece is in use is $P_2$, the pressure of lubricating oil sealed in the oil case 1 is $P_3$ and the pressure of air inside the air feed pipe 2 when the hand-piece is not in use is $P_4$, the spring pressure $P_1$ is set in the range in which the following inequality is established:

$$P_2 > P_1 + P_3 P_4 \tag{1}$$

Accordingly, when the hand-piece is not in use, the lubricating oil is completely prevented from flowing into the air feed pipe 2 because the ball valve 32 is always pressed against the oil port 21 of the air feed pipe 2 by the spring pressure $P_1$ of the coil spring 33 and by the lubricating oil pressure $P_3$ as shown in FIG. 2. In contrast thereto, when the hand-piece is in use, the ball valve 32, because the pressure $P_2$ of rotor driving air is greater than the total pressure of the spring pressure $P_1$ and the lubricating oil pressure $P_3$, is always pressed down to an open state, so that the lubricating oil comes into contact with the rotor driving air which flows in through the oil port 21 as shown by arrow F and is continuously mixed with the air, continuously atomized by the flow rate of the air, and fed to the rotor together with the air. Additionally, the adjustment of the amount of lubricating oil mixed and of the mist grain size is effected by adjusting the diameter of the oil port 21. Since in the case of ordinary dental hand-piece device, the rotor driving air flows through the air pipe 2 (usually on the order of 2-2.5 mm in inner diameter) under a pressure of about 2.0–4.0 kg/cm² and at a flow rate of about 20–40 l/min., it is desirable that the oil port 21 is usually on the order of 1 mm in diameter.

Also, the oil case 1 is not placed under any restriction with respect to the quality and size of material used, but preferably it should be made of transparent or semitransparent synthetic resin so as to permit the confirmation of the amount of oil left of the lubricating oil. What is better, a lubricating oil filling or refilling port is formed at a suitable spot (for example, the peripheral walls of oil case shown or thick-walled portion at the other end of the oil case), and a check valve similar in construction to the aforestated check valve (but it is not necessary to satisfy the aforestated condition concerning the coil spring) is mounted to the port to permit the free filling or refilling of oil from suitable lubricating oil cylinder.

Next, the small-sized oiler A' shown in FIGS. 3 and 4 is of an internally mounted type in which the oiler is detachably attached to the hand-piece adjacent to the end of the head thereof by a means such as threading or molding so as to form part of the hand-piece and is designed to facilitate dentist's delicate cutting operation by bringing the hand-piece into a compact form. This small-sized oiler is the same in the construction of the essential part as the small-sized oiler mounted to the rear end thereof except that an exhaust pipe 8 is loosely inserted through and fixed to the oil case 1 and that the check valve 7 for filling or refilling oil is embedded in the thick-walled portion at the other end of the oiler, and hence a more detailed description is omitted to avoid repetition. Incidentally, it should be understood that the small-sized oiler of the first-mentioned type in which it is connected to the rear end of the hand-piece, if a special hand-piece capable of detachably receiving the oiler thereinto is separately produced, can be used as an internally mounted type small-sized oiler without any further modification.

On the other hand, the mist lubrication method of the invention provides continuous lubrication through the supply of mist oil together with air to the rotor by use of the above mentioned small-sized oiler mounted detachably in a position (for example, inside or at the rear end of the hand-piece) adjacent to the rotor side of the rotor driving air feed passageway of the dental hand-piece and by use of the pressure and flow rate of the rotor driving air during the use of the hand-piece so as to mix continuously lubricating oil from the oiler into the air and to atomize the same. The rotor driving air is supplied to the rotor under the same condition as it is supplied to an ordinary dental hand-piece, the pressure and flow rate of the air being on the order of 2.0–4.0 kg/cm² and on the order of 250–320 m/sec. respectively. The amount of lubricating oil mixed is preferably adjusted to be usually in the range of 0.002–0.02 cc/min. And there is a possibility that if the amount of oil is below the range, oil shortage causes bad lubrication while conversely a larger amount causes seizure of the excessive oil to the rotor. In atomizing the oil, it is desirable to adjust the mixing so as to obtain micron grain of a micron order (usually 2–5μ). Such micron grain provides an excellent lubrication effect. As mentioned previously, adjustment of the amount of lubricating oil mixed and adjustment of mist grain are carried out by adjustment of the diameter of oil port 21.

The lubrication method of the invention described above provides the following marked effects. Firstly, because the use of the small-sized oiler makes it possible to mix and atomize the lubricating oil automatically and continuously by making use of the pressure and flow rate of the rotor driving air used for the hand-piece in operation, constant lubrication can be continuously carried out. Secondly, lubrication by mere mounting of the oiler to the inside or the rear end of the hand-piece increases working efficiency such as mounting, exchange or the like. Thirdly, when the oil case is made of transparent or semitransparent material, the amount of oil left unused can always be confirmed, and hence there is no possibility of the oil shortage causing seizure of the rotor. Fourthly, the use of the small-sized oil cylinder or the like. Fifthly, the low cost of manufacture of the oiler is advantageous in point of economy. Sixthly, because the small-sized oiler can be attached by the dentist to the inside or the rear end of the hand-piece, it poses no problem such as there was in connection with the space and cost of installation of the conventional large-sized atomizer. Seventhly, if the hand-piece is used in the manner that when an air bearing type hand-piece is used, the hand-piece is used without mounting of the oiler and that only when a ball bearing type hand-piece is used, the oiler is mounted a single rotor driving air feed passageway may be used both for the air bearing type hand-piece and for the ball bearing type hand-piece.

As described above, the lubricating method and small-sized oiler of the invention are highly useful and contribute their great share to the field of dental treatment.

We claim:

1. A small-size oiler in combination with a dental hand-piece including an oil case detachably coupled to said dental hand-piece, an air feed pipe detachably coupled to a rotor driving air passageway of said dental hand-piece, said pipe being loosely inserted into and fixed to said oil case, and an oil check valve coupled to an oil port in said feed pipe, said check valve being automatically opened by the pressure and flow rate of the rotor driving air flowing through said air feed pipe to thereby cause the lubricating oil in the oil case to be continuously mixed into said air and atomized.

2. A small-sized oiler according to claim 1 wherein the oiler is designed to be detachably connected to the rear end portion of the dental hand-piece.

3. A small-sized oiler according to claim 1 wherein the oiler is designed to be detachably mounted inside the dental hand-piece.

4. A small-sized oiler according to claims 1, 2 or 3 wherein the oiler case is made of material whereby the amount of oil left unused can be checked through the case.

5. A small-sized oiler according to claims 1, 2, or 3 wherein the oil case is provided with a check valve for filling and refilling lubricating oil.

6. A dental hand-piece of the type including a rotor driving air feed pipe having an input provided in an end of said dental hand-piece in combination with a small-size oiler, said oiler comprising an oil case detachably coupled to said dental hand-piece, an air feed pipe detachably coupled to said input of said rotor driving air feed pipe in said end of said dental hand-piece, said pipe loosely inserted into and fixed to said oil case, and an oil check valve coupled to an oil port in said feed pipe, said check valve being automatically opened by the pressure and flow rate of the rotor driving air flowing through said air feed pipe to thereby cause the lubricating oil case to be continuously mixed into said air and atomized.

7. A small size continuously oiling oiler for use with a dental hand-piece comprising an oil case, an air feed pipe loosely provided in and fixed to said oil case, and an oil check valve provided in an oil port in said air feed pipe, said check valve being automatically opened by the pressure and flow rate of the rotor driving air flowing through said air feed pipe to thereby cause the lubricating oil in said oil case to be continuously mixed into said air and atomize as said air flows through said air feed pipe.

8. A small size continuously oiling oiler according to claim 7 wherein said check valve exerts a biasing force $P_1$ in accordance with the formula as follows:

$$P_2 > P_1 + P_3 > P_4$$

wherein $P_2$ is the pressure of the rotor driving air inside said air feed pipe, $P_3$ is the pressure of lubricating oil in said oil case and $P_4$ is the pressure of the air inside the air feed pipe when air is not flowing through the air feed pipe.

* * * * *